US011517520B2

(12) United States Patent
Bardey et al.

(10) Patent No.: US 11,517,520 B2
(45) Date of Patent: Dec. 6, 2022

(54) **USE OF A *NEPHELIUM LAPPACEUM* EXTRACT FOR INCREASING THE FIRMNESS OF THE SKIN AND/OR OF THE MUCOUS MEMBRANES**

(71) Applicant: BASF BEAUTY CARE SOLUTIONS FRANCE SAS, Lyons (FR)

(72) Inventors: Vincent Bardey, Nancy (FR); Isabelle Bonnet, Lyons (FR); Anabelle Echard, Luneville (FR); Nicolas Pelletier, Lyons (FR); Boris Vogelgesang, Lyons (FR)

(73) Assignee: BASF BEAUTY CARE SOLUTIONS FRANCE SAS, Lyons (FR)

( * ) Notice: Subject to any disclaimer, the term of this patent is extended or adjusted under 35 U.S.C. 154(b) by 0 days.

(21) Appl. No.: 16/610,942

(22) PCT Filed: May 3, 2018

(86) PCT No.: PCT/FR2018/051095
§ 371 (c)(1),
(2) Date: Nov. 5, 2019

(87) PCT Pub. No.: WO2018/203000
PCT Pub. Date: Nov. 8, 2018

(65) Prior Publication Data
US 2020/0078291 A1 Mar. 12, 2020

(30) Foreign Application Priority Data
May 5, 2017 (FR) ...................................... 1753987

(51) Int. Cl.
| | | |
|---|---|---|
| *A61K 36/00* | (2006.01) | |
| *A61K 8/9789* | (2017.01) | |
| *A61P 17/00* | (2006.01) | |
| *A61K 36/77* | (2006.01) | |
| *A61Q 19/06* | (2006.01) | |
| *A61Q 19/08* | (2006.01) | |
| *A61K 9/00* | (2006.01) | |

(52) U.S. Cl.
CPC ............ *A61K 8/9789* (2017.08); *A61K 36/77* (2013.01); *A61P 17/00* (2018.01); *A61Q 19/06* (2013.01); *A61Q 19/08* (2013.01); *A61K 9/0014* (2013.01); *A61K 9/0053* (2013.01); *A61K 2236/33* (2013.01); *A61K 2800/78* (2013.01)

(58) Field of Classification Search
None
See application file for complete search history.

(56) References Cited

U.S. PATENT DOCUMENTS

| | | |
|---|---|---|
| 2004/0096925 A1 | 5/2004 | Perrier et al. |
| 2007/0184012 A1 | 8/2007 | Perrier et al. |
| 2010/0040710 A1 | 2/2010 | Perrier et al. |

FOREIGN PATENT DOCUMENTS

| | | | |
|---|---|---|---|
| CA | 2346384 A1 | 4/2000 | |
| EP | 1119344 B1 | 12/2004 | |
| FR | 2847267 A1 | 5/2004 | |
| FR | 2855968 A1 | 12/2004 | |
| FR | 2893252 A1 | 5/2007 | |
| FR | 2907014 A1 | 4/2008 | |
| FR | 2941373 A1 | 7/2010 | |
| GB | 2443036 A | 4/2008 | |
| JP | 2002145730 A | 5/2002 | |
| JP | 2011006333 A | 1/2011 | |
| KR | 20060007083 A | 1/2006 | |
| KR | 20090056521 A | 6/2009 | |
| WO | WO-2005120554 A1 | 12/2005 | |
| WO | WO-2008066370 A1 * | 6/2008 | ............. A61P 39/06 |
| WO | WO-2010014861 A1 | 2/2010 | |

(Continued)

OTHER PUBLICATIONS

Masaki (2010) J. Dermatological Science, 58: 85-90. (Year: 2010).*
Ballosteros et al. (2017) Food Chemistry 237: 623-631. (Year: 2017).*
Largo et al. (2015) Rev. Fac. Nat. Agr. Medillin 68(1): 7509-7520. (Year: 2015).*
Di Battista et al. (2015) Powder Technology 286: 193-201. (Year: 2015).*
Sukmandori et al. (2017) Research J. Pharm. and Tech. 10(8): 9 pages. (Year: 2017).*

(Continued)

*Primary Examiner* — Russell G Fiebig
(74) *Attorney, Agent, or Firm* — Faegre Drinker Biddle & Reath LLP

(57) ABSTRACT

The invention relates to the use of various extracts of the *Nephelium lappaceum* plant for increasing the firmness and/or elasticity of the skin and/or mucous membranes, by increasing type I and/or type V collagen and/or LOX-L, fibulin-5, emiline-1 and/or fibrillin-1 gene and/or protein expression, and/or by decreasing CYR61 expression, in the skin and mucous membranes. Another subject of the invention relates to the use of said extracts in a cosmetic composition comprising at least one cosmetically acceptable excipient. Another subject further relates to a cosmetic care method comprising the application of the extract according to the invention or of a cosmetic composition comprising it, for increasing the firmness and/or elasticity of the skin and/or mucous membranes, by increasing type I and/or type V collagen, fibrillin-1 and/or LOX-L, fibulin-5, emiline-1 and/or fibrillin-1 gene and/or protein expression, and/or by decreasing CYR61 expression, in the skin and mucous membranes. A final subject relates to an *N. lappaceum* extract for use thereof, alone or in a dermatological or pharmaceutical composition, in the prevention and/or treatment of pathological conditions involving a loss of collagen protein and/or gene expression and/or a pathological loss of firmness of the skin and/or mucus membranes, such as rosacea and telangiectasia.

10 Claims, No Drawings

(56) References Cited

FOREIGN PATENT DOCUMENTS

WO   WO-2010063674 A1   6/2010
WO   WO-2014170347 A1   10/2014

OTHER PUBLICATIONS

Kim et al. (2017) Intern. J. Biol. Macromolecules 104: 631-637. (Year: 2017).*
Pandel et al. (2013) ISRN Dermatology, Article ID: 930164 (11 pages). (Year: 2013).*
Sansone et al. (2011) J. Food Engineering 105: 468-476. (Year: 2011).*
Sommerfeld (2007) Phytomedicine 14: 711-715. (Year: 2007).*
Ariffin, N.H., et al., "Potential Dermatological Application on Asian Plants", Biotechnology and Bioprocess Engineering, vol. 21, No. 3, (2016), pp. 337-354.
International Premliminary Report on Patentability for PCT/FR2018/051095 dated Jul. 10, 2018.
Lourith, N., et al., "In vitro and cellular activities of the selected fruits residues for skin aging treatment", Anais da Academia Brasileira de Ciências, vol. 89, No. 1 Supplement, (2017), pp. 577-589.
Orwa, C., et al., "*Nephelium lappaceum* (Rambutan)", Agroforestree Database: a Tree Reference and Selection Guide Version 4.0, (2009), pp. 1-5, XP055429429.
Palanisamy, U., et al., "Rind of the rambutan, Nephelium lappaceum, a potential source of natural antioxidants", Food Chemistry, vol. 109, No. 1, (2007), pp. 54-63.
Sekar, M., et al., "Formulation and Evaluation of Novel Antiaging Cream Containing Rambutan Fruits Extract", International Journal of Pharmaceutical Sciences and Research, vol. 8, No. 3, (2017), pp. 1056-1065.
XP002776210, Database Global New Products Database (GNPD) MINTEL, Accession No. 1606102, Tonymoly: "Hot Body Gel", Aug. 1, 2011.
XP002776211, Database Global New Products Database (GNPD) MINTEL, Accession No. 1349546, Tonymoly: "Eye Cream", Jun. 1, 2010.
XP002776212, Database Global New Products Database (GNPD) MINTEL, Accession No. 4635695, GlamGlow: "Matte Lip Treatment", Feb. 1, 2017.
Yuslanti, E.R., et al., "Effect of Rambutan-honey and its Flavonoid on TGF-β1 Induce Fibroplasia Oral Wound Healing", Research Journal of Medicinal Plants, vol. 10, No. 8, (2016), pp. 435-442.
Zanetti, M., et al., "EMILIN-1 Deficiency Induces Elastogenesis and Vascular Cell Defects", Molecular and Cellular Biology, vol. 24, No. 2, (2004), pp. 638-650.

\* cited by examiner

USE OF A *NEPHELIUM LAPPACEUM* EXTRACT FOR INCREASING THE FIRMNESS OF THE SKIN AND/OR OF THE MUCOUS MEMBRANES

CROSS-REFERENCE TO RELATED APPLICATIONS

This application is a national stage application (under 35 U.S.C. § 371) of PCT/FR2018/051095, filed May 3, 2018, which claims benefit of French Application No. 175398), filed May 5, 2017, both of which are incorporated herein by reference in their entirety.

The present invention relates to the field of cosmetics and dermatology, in particular the novel cosmetic and/or dermatological use of an extract of the *Nephelium lappaceum* plant for increasing the firmness and/or the elasticity of the skin and/or mucous membranes.

Collagen is a major constituent protein of the extracellular matrix (ECM) present in large amounts in vertebrate tissues. It is part of a superfamily of 29 distinct members, including fibrillar collagens. Type I collagen is the best known example thereof, but type V collagen is also a fibrillar collagen. Type V collagen is found in the same tissues as type I collagen, and is known to aid the assembly of heterogeneous fibers composed of these 2 types of collagen. They thus ensure the maintaining of the structures and gives the tissues their mechanical strength. Thus, at the level of the dermis, it contributes to the firmness of these tissues, and therefore to the firmness of the skin.

During intrinsic aging of tissues, particularly of the dermis and the epidermis, the collagen expression decreases, inducing a relaxation of these tissues, and therefore a loss of tone and of firmness of the skin. Various extrinsic factors are also responsible for loss of firmness of the skin and/or mucous membranes, including aggressive environmental agents such as UV radiation, pollution or tobacco. Other intrinsic factors may also be responsible for disorganization of collagen fibers and a decrease in firmness, in particular hormonal variations, and changes in tension in the skin and/or mucous membranes (rapid weight gain or loss).

Fibrillin-1 is, for its part, also a protein synthesized by fibroblasts, which is a constituent of the ECM in the dermis. It participates in the formation of elastic fibers consisting of elastin.

Just like collagen, the expression of this protein decreases during aging of the skin and/or other intrinsic factors, in particular hormonal factors, and extrinsic factors, in particular environmental factors, inducing a relaxation of elastic tissues.

Another protein participates in the formation of elastic fibers, LOX-L (Lysyl oxidase-like). This enzyme allows the crosslinking of tropoelastin, which is then deposited at the microfibrils. Like collagen and fibrillin-1, its expression will decrease over time in the skin and mucous membranes. Lastly, mention may be made of the (CYR61 (Cysteine rich angiogenic inducer 61) proteins which regulate certain syntheses of the ECM: fibulin-5 which is a constituent of elastic fibers or else emilin-1, which is a glycoprotein of the ECM associated with elastic fibers. The formation and correct arrangement of the elastic fibers will depend on the level of expression of the proteins mentioned above.

These proteins, collagen I, collagen V, fibrillin-1, CYR61, emilin-1, fibulin-5 and LOX-L are therefore preferred targets in the field of cosmetics and dermatology, which fields constantly demand alternative active ingredients to combat the loss of firmness and/or elasticity.

In a particularly surprising manner, the inventors have discovered that an extract of the *Nephelium lappaceum* plant has the property of increasing the firmness of the skin and/or mucous membranes, in particular by increasing type I and/or type V collagen gene and/or protein expression, in the skin and mucous membranes, but also of increasing the elasticity of the skin and/or mucous membranes, in particular by increasing fibrillin-1, LOX-L, fibulin-5 and emilin-1 gene and/or protein expression.

The extract according to the invention is an extract of the *N. lappaceum* plant. This tree, also known as rambutan, is found in southeast Asia, in particular in Malaysia and Indonesia. It is a tree 10 to 20 meters high, producing a large amount of fruit. This edible fruit is known for its organoleptic properties; it contains high amounts of sugars, vitamin C and iron. Decoctions of roots or dried leaves have also been used to combat fever.

The plant from which the extract according to the invention is prepared originates from Vietnam.

The extract according to the invention has the advantage of being effective on several types of collagens: type I and type V collagen. The extract therefore makes it possible to increase the firmness of the skin and/or mucous membranes by increasing type I collagen gene and/or protein expression, while in addition increasing the expression of other ECM components such as type V collagen or decreasing CYR61 expression. Yet another advantage of the extract according to the invention is that it makes it possible to increase the elasticity of the skin and/or mucous membranes by increasing the gene and/or protein expression of fibrillin-1 but also of LOX-L, fibulin-5 and emilin-1. This extract therefore makes it possible to target several types of ECM proteins, by making a complete cosmetic and/or dermatological ingredient.

The extract according to the invention also has the advantage of being an ingredient that can be easily formulated and that can easily be manufactured on an industrial scale. It is a topically acceptable active ingredient for the skin and mucous membranes, which does not present a risk of allergy.

A commercial body gel having a firming effect and comprising 10 plant extracts, including an *N. lappaceum* extract, has been described. However, the ingredient that is active on firmness is a pepper extract comprising capsaicin and no activity on firmness, in particular chosen from firmness, anti-cellulite activity and slimming activity, is associated with the *N. lappaceum* extract. Application KR20060007083 describes a cosmetic composition comprising an *N. lappaceum* extract, said composition being used as a skin-whitening agent.

Extracts of the plant, prepared by extraction in various solvents including ethanol, have been described for their free-radical scavenger activity in application WO 2008/066370. Similarly, application JP2002145730 discloses several effects, including a moisturizing and antioxidant effect, of the seeds of the *N. lappaceum* plant.

Lourith et al. (2017, Anais da Academia Brasileira de Ciencias, 89, 577-589) describes, moreover, extracts of lychee (*Litchi chinensis*) pericarp and of *N. lappaceum* as possessing anti-collagenase activity. However, nowhere in this document is described the use of an *N. lappaceum* extract for increasing the firmness of the skin, or for increasing type I or type V collagen expression in particular. There is also no mention of an extract of *N. lappaceum* leaves. In addition, this document refers to the preferential use of the lychee extract in anti-aging cosmetic products, rather than the *N. lappaceum* extract.

Finally, application KR20090056521 describes an extract of *N. lappaceum* and lychee (*Litchi chinensis*) in a cosmetic composition for the skin, having an anti-wrinkle effect and making it possible to inhibit collagen degradation by metalloproteinases (MMPs), in particular MMP-1s. However, no effect of increasing type I or V collagen protein and/or gene expression using an *N. lappaceum* extract, in particular using a leaf extract, is described in this prior art. There is also no disclosure of an effect on increasing the firmness of the skin using this extract in this patent application. Moreover, it describes an effect of inhibiting proteinases responsible for collagen degradation, but not an increase in type I or type V collagen expression in particular. Thus to the knowledge of the applicant, no document describes the use of an extract of the *N. lappaceum* plant for increasing the firmness or elasticity of the skin and/or mucous membranes or for increasing the expression of type I and type V collagen, fibulin-1, emilin-1, LOX-L and/or fibrillin, and/or decreasing CYR61 expression, in the skin and/or mucous membranes.

Thus, according to a first subject, the invention relates to the cosmetic use of an *N. lappaceum* extract for increasing the firmness of the skin and/or mucous membranes.

According to a second subject, the invention relates to the cosmetic use of an *N. lappaceum* extract for increasing the elasticity of the skin and/or mucous membranes. For the purposes of the invention, a distinction is in fact made between effectiveness on firmness and effectiveness on the elasticity of the skin and/or mucous membranes. Firmness is closely related to the density of the extracellular matrix, in particular but not exclusively to collagen expression. Elasticity is related to the formation and assembly of elastic fibers, in which the fibrillin-1, LOX-L, fibulin-5 and emilin-1 proteins participate.

For the purposes of the present invention, the term "cosmetic use" is intended to mean nontherapeutic use, that is to say intended to be applied to all or part of a healthy, non-pathological, area of skin or mucous membrane. The expression "area of healthy skin and/or healthy mucous membrane" is intended to mean an area of the skin and/or mucous membrane to which the extract according to the invention is applied and which is referred to as "non-pathological" by a dermatologist, that is to say which does not have an infection, scar, skin disease or disorder such as candidiasis, impetigo, psoriasis, eczema, acne or dermatitis, or wounds or injuries and/or other dermatoses.

The extract according to the invention may be applied to all or part of the skin of the body and/or the face where the increase in firmness and/or elasticity is desired, preferentially the legs, thighs, arms, stomach, bust, neck, all or part of the face, preferentially the cheeks, forehead, chin, lips, area around the lips, area around the eyes, the "T" zone of the face. For the purposes of the present invention, the skin includes the scalp.

For the purposes of the present invention, the term "collagen" is intended to mean type I, III, IV, V, VI, VII, XII, XIII, XIV, XVI, XVII, XVIII, XXIV and/or XXIX collagen present in the skin and/or mucous membranes. Preferentially according to the invention, it is type I and/or V collagen, even more preferentially type I collagen.

The term "fibrillin" is, moreover, intended to mean fibrillin-1, fibrillin-2 and/or fibrillin-3, preferentially fibrillin-1 present in the skin and/or mucous membranes.

The *N. lappaceum* extract according to the invention is a topically acceptable ingredient. The term "topically acceptable" is intended to mean an ingredient suitable for topical application, which is non-toxic, non-irritating to the skin and/or mucous membranes, which does not induce an allergic response, and which is not chemically unstable. The extract according to the present invention may be used orally or topically. Advantageously, it is used topically. The term "topically" is intended to mean the direct local application and/or spraying of the ingredient onto the surface of the skin and/or mucous membranes.

The term "mucous membrane" is intended to mean the ocular mucous membrane, the vaginal mucous membrane, the urogenital mucous membrane, the anal mucous membrane, the nasal mucous membrane and/or the oral, labial and/or gingival mucous membrane; preferentially, the labial and/or oral mucous membranes.

For the purposes of the present invention, the term "increase the firmness of the skin and/or mucous membranes" is intended to mean an increase in firmness of the skin and/or mucous membranes of at least 1%, preferentially of at least 3%, more advantageously of at least 5% in the presence of an *N. lappaceum* extract according to the invention. In one advantageous embodiment of the invention, it is an increase measured in vivo, preferentially on the skin of the human face. Even more preferentially, this increase in the firmness of the skin of the human face is measured after application of a cream comprising an extract of *N. lappaceum* leaves, preferentially present in an amount of 0.1% by weight relative to the total weight of the cream. Alternatively, the leaf extract will be present in an amount of 2% by weight relative to the total weight of the cream. In this case, it will be an extract prepared in water in subcritical conditions under the conditions described in example 1e).

In one advantageous embodiment of the invention, the cream is applied to a half of the face of a population of 30 women aged 55 to 65 years, and the measurement of the increase in firmness is carried out after 28 and 56 days of daily application of said cream, in comparison with the application under the same conditions of a placebo cream that does not comprise the extract of *N. lappaceum* leaves.

The in vivo measurement of the firmness may be carried out according to the conventional methods known to those skilled in the art, in particular by measuring with a cutometer, a Tonoderm™, a DynaSKIN® associated with a demaTOP or by means of a device named SkinFibroMeter (Delfin). In one particularly advantageous embodiment of the invention, the firmness is evaluated by measuring the distribution of the volumes of the skin subjected to pressure deformation of the SkinFibroMeter, making it possible to evaluate the biomechanical properties of the skin.

The term "increasing the elasticity" of the skin and/or mucous membranes is also intended to mean an increase in the elasticity measured in vivo of at least 2%, advantageously of at least 4%, and more advantageously of at least 6% in the presence of the extract according to the invention, relative to the elasticity detected in the absence of the extract. In one preferential embodiment of the invention, this measurement is carried out on the skin of the human face. Even more preferentially, the increase in the elasticity of the skin of the human face is measured in the presence of a cream comprising an extract of *N. lappaceum* leaves, advantageously present in an amount of 1% by weight relative to the total weight of the cream. Alternatively, the leaf extract will be present in an amount of 2% by weight relative to the total weight of the cream. In this case, it will be an extract prepared in water in subcritical conditions under the conditions described in example 1e).

In one advantageous embodiment of the invention, the cream is applied to a half of the face of a population of 30 women aged 55 to 65 years, and the measurement of the elasticity is carried out after 28 and 56 days of daily application of said cream, in comparison with the application under the same conditions of a placebo cream that does not comprise the extract of *N. lappaceum* leaves. The measurement of the elasticity may be carried out using a ballistometer, a corneometer or a cutometer. In one advantageous embodiment, it will be measured by cutometry, a technique for measuring the mechanical strain of the skin subjected to suction.

The method referred to as fringe projection will make it possible to measure the wrinkles in vivo. Thus, in the context of the present invention, the term "decreasing the wrinkles" is intended to mean a reduction of at least 0.5%, preferentially of at least 1%, more preferentially of at least 2% of fine wrinkles in the presence of the extract according to the invention with respect to the level of fine wrinkles measured in the absence of the extract. In one preferential embodiment of the invention, this measurement is carried out on the skin of the human face. Even more preferentially, the decrease in the fine wrinkles of the skin of the human face is measured in the presence of a cream comprising an extract of *N. lappaceum* leaves, advantageously present in an amount of 1% by weight relative to the total weight of the cream. Alternatively, the leaf extract will be present in an amount of 2% by weight relative to the total weight of the cream. In this case, it will be an extract prepared in water in subcritical conditions under the conditions described in example 1e).

In one advantageous embodiment of the invention, the cream is applied to a half of the face of a population of 30 women aged 55 to 65 years, and the measurement of the fine wrinkles is carried out after 28 and 56 days of daily application of said cream, in comparison with the application under the same conditions of a placebo cream that does not comprise the extract of *N. lappaceum* leaves.

In one advantageous embodiment of the invention, the *N. lappaceum* extract is not combined with any extract of the *L. chinensis* plant. In particular, the extract according to the invention is preferentially not combined with an extract of *L. chinensis* fruit.

Likewise, the extract according to the invention is preferentially not combined with capsaicin (CAS number 404-86-4, molar mass 305.418 g/mol) or any plant extract comprising it. In particular, the extract according to the invention is not combined with a fruit extract of any plant species of the *Capsicum* genus comprising capsaicin.

An object of the present invention is therefore the cosmetic use of an *N. lappaceum* extract for increasing the firmness and/or elasticity of the skin and/or mucous membranes, by increasing type I collagen, type V collagen, emilin-1, fibulin-5 and fibrillin, preferentially fibrillin-1, and/or LOX-L gene and/or protein expression, and/or by decreasing CYR61 expression.

In particular, a subject of the present invention is therefore the cosmetic use of an *N. lappaceum* extract for increasing the firmness of the skin and/or mucous membranes, by increasing type I and/or type V collagen gene and/or protein expression and/or decreasing CYR61 expression. Another particular subject of the present invention is the cosmetic use of an *N. lappaceum* extract for increasing the elasticity of the skin and/or mucous membranes, by increasing emilin-1, fibulin-5, fibrillin, preferentially fibrillin-1, and/or LOX-L gene and/or protein expression.

In the context of the invention, the term "gene increase" is intended to mean an increase in the mRNAs encoding the protein of interest.

For the purposes of the present invention, the expression "increasing collagen gene and/or protein expression" is intended to mean an increase in collagen protein and/or gene expression of at least 4%, preferentially of at least 20%, even more preferentially of at least 50%, advantageously of at least 100%, and very advantageously of at least 400%, in the presence of the *N. lappaceum* extract according to the invention, with respect to the collagen protein and/or gene expression detected in the absence of the extract.

In one advantageous embodiment of the invention, the collagen expression is the protein expression of type I and/or type V collagen, more preferentially of type I collagen. Preferentially, said expression is measured in human fibroblasts described as normal, that is to say non-pathological, more preferentially in the presence of an *N. lappaceum* extract according to the invention, advantageously in the presence of extract 1a) or extract 1e).

Preferentially, the type I and/or type V collagen protein expression is measured by immunohistochemical technique using an anti-collagen antibody as described under the conditions of example 2.

In one particularly advantageous embodiment of the invention, an extract of *N. lappaceum* leaves is used to increase the firmness of the skin and/or mucous membranes by increasing type I and/or type V, preferentially type I, collagen gene and/or protein expression, preferentially protein expression.

In an alternative embodiment of the invention, an extract of *N. lappaceum* leaves is used to increase the firmness of the skin and/or mucous membranes by decreasing CYR61 gene and/or protein expression, preferentially protein expression.

The expression "decreasing CYR61 gene and/or protein expression" is intended to mean a decrease in gene and/or protein expression of at least 4%, preferentially of at least 15%, more preferentially of at least 30% in the presence of the *N. lappaceum* extract according to the invention, with respect to the level of CYR61 protein and/or gene expression detected in the absence of the extract.

In one advantageous embodiment, the decrease is a decrease in CYR61 protein expression, advantageously measured in normal, i.e. non-pathological, human fibroblasts, more preferentially measured in the presence of an *N. lappaceum* extract according to the invention, very advantageously in the presence of extract 1a) or 1e), under the conditions described in example 5. In addition, the expression "increasing fibrillin gene and/or protein expression" is intended to mean increasing fibrillin protein and/or gene expression by at least 30%, preferentially by at least 50%, more preferentially by at least 100%, advantageously by at least 150% and very advantageously by at least 200% in the presence of the *N. lappaceum* extract according to the invention with respect to the level of fibrillin protein and/or gene expression detected in the absence of the extract. In one advantageous embodiment, it is a question of increasing fibrillin-1 protein expression, advantageously measured in normal, i.e. non-pathological, human fibroblasts, more preferentially measured in the presence of an *N. lappaceum* extract, advantageously in the presence of extract 1a) or extract 1e), under the conditions described in example 4.

Thus according to the invention, the *N. lappaceum* extract is used for increasing the elasticity of the skin and/or mucous membranes, by increasing fibrillin expression, advantageously fibrillin-1 expression.

In an alternative embodiment of the invention, the *N. lappaceum* extract is used for increasing the elasticity of the skin and/or mucous membranes by increasing LOX-L gene and/or protein expression. For the purposes of the invention, the expression "increasing LOX-L gene and/or protein expression" is intended to mean an increase of at least 2%, preferentially of at least 5%, more preferentially of at least 10% and very preferentially of at least 15% of the LOX-L gene and/or protein expression in the presence of the *N. lappaceum* extract according to the invention with respect to the level of LOX-L protein and/or gene expression detected in the absence of the extract. In one advantageous embodiment, the increase is an increase in LOX-L protein expression, advantageously measured in normal, i.e. non-pathological, human fibroblasts, more preferentially measured in the presence of an *N. lappaceum* extract according to the invention, very advantageously in the presence of extract 1a) or 1e).

In another alternative embodiment of the invention, the extract increases the elasticity of the skin and/or mucous membranes by increasing fibulin-5 gene and/or protein expression. For the purposes of the invention, the expression "increasing fibulin-5 gene and/or protein expression" is intended to mean an increase of at least 2%, preferentially of at least 5%, more preferentially of at least 10% and very preferentially of at least 15% of fibulin-5 gene and/or protein expression in the presence of the *N. lappaceum* extract according to the invention, with respect to the level of fibulin-5 protein and/or gene expression detected in the absence of the extract. In one advantageous embodiment, the increase is an increase in fibulin-5 protein expression, advantageously measured in normal, i.e. non-pathological, human fibroblasts, more preferentially measured in the presence of an *N. lappaceum* extract according to the invention, very advantageously in the presence of extract 1a) or 1e).

In yet another alternative embodiment of the invention, the extract increases the elasticity of the skin and/or mucous membranes by increasing emilin-1 gene and/or protein expression. For the purposes of the invention, the expression "increasing emilin-1 gene and/or protein expression" is intended to mean an increase in emilin-1 protein and/or gene expression of at least 2%, preferentially of at least 5%, more preferentially of at least 10% and very preferentially of at least 15% in the presence of the *N. lappaceum* extract according to the invention with respect to the level of emilin-1 protein and/or gene expression detected in the absence of the extract. In one advantageous embodiment, the increase is an increase in emilin-1 protein expression, advantageously measured in normal, i.e. non-pathological, human fibroblasts, more preferentially measured in the presence of an *N. lappaceum* extract according to the invention, very advantageously in the presence of extract 1a) or 1e).

A subject of the present invention is therefore the cosmetic use of an *N. lappaceum* extract for increasing the elasticity of the skin and/or mucous membranes, by increasing fibrillin-1, LOX-L, fibulin-5 and/or emilin-1 gene and/or protein expression. In one advantageous embodiment of the invention, an extract of leaves and/or branches and/or bark and/or stem and/or seeds, preferentially leaves, of *N. lappaceum* is used for increasing fibrillin-1, LOX-L, fibulin-5 and/or emilin-1 gene and/or protein expression, preferentially fibrillin-1 gene and/or protein expression, more preferentially fibrillin-1 protein expression, to increase the elasticity of the skin and/or mucous membranes.

The extract may be all or part of the *N. lappaceum* plant chosen from the bark, leaves, branches, stem, whole fruit, fruit pulp, seeds, pericarp, root. Preferentially according to the invention, the extract is a leaf and/or seed and/or pulp and/or branch extract. More preferentially, the extract is a leaf extract. The whole plant or the part of the plant in question is preferentially dried and/or milled before extraction.

For the purposes of the present invention, the term "pulp" is intended to mean the fruit without the pericarp and without the seed. The term "pericarp" is intended to mean the envelope of the fruit, also referred to as the shell. The term "bark" is also intended to mean the bark of the tree and/or of the branches. Thus, the term "branch" is intended to mean the wood and the bark. The term "seed" is intended to mean the seed without the pulp.

The extract can be obtained by various extraction methods known to those skilled in the art, chosen from maceration, hot decoction, by milling including ultrasonic milling, using a mixer, or else the extract can be obtained by extraction in water under subcritical conditions. Preferentially, the extraction is carried out by maceration. In one particularly advantageous embodiment, the extraction is carried out in water under subcritical conditions. Advantageously, the extraction is not carried out under supercritical conditions ($CO_2$).

The extraction may be carried out at a temperature ranging from 4° C. to 300° C., including ambient temperature, that is to say a temperature of 20° C. In one preferential embodiment of the invention, the extraction will be carried out at a temperature of from 60° C. to 90° C., preferentially from 70° C. to 85° C., more preferentially at a temperature of 80° C.

In one alternative embodiment of the invention, the extraction will be carried out at a temperature of from 4° C. to 25° C., more preferentially from 4° C. to 20° C., more advantageously at ambient temperature, that is to say at 20° C.

In yet another alternative embodiment of the invention, the extraction will be carried out in water under subcritical conditions, at a temperature ranging from 100° C. to 374° C., advantageously from 120° C. to 250° C., more advantageously at 120° C. The extraction can be carried out at a single given temperature or at successive increasing temperatures. In one advantageous embodiment of the invention, the extraction will be carried out sequentially at three increasing temperatures of 120° C., 140° C. and 160° C.

The term extraction under "subcritical conditions" is intended to mean extraction in the presence of water, under conditions of temperature greater than 100° C. and pressure less than 221 bar, such that the water remains in the liquid state but has a viscosity and a surface tension lower than that of water at ambient temperature, increasing its dielectric constant.

Thus, the extraction pressure will between 150 bar and 250 bar, preferentially between 200 and 221 bar, advantageously in a pressure extraction autoclave.

The extraction can be carried out for a period of from 30 minutes to 24 hours, preferentially from 30 minutes to 12 hours, more preferentially for a period of from 1 hour to 5 hours, and more advantageously for a period of from 1 hour to 2 hours. Very advantageously, the extraction will be carried out for a period of 1 hour.

The extract according to the invention may be obtained by extraction in a solvent or solvent mixture, preferably a protic polar solvent, and advantageously in water, an alcohol, a glycol, a polyol, a water/alcohol, water/glycol or water/polyol mixture (such as water mixed with ethanol, glycerol and/or butylene glycol and/or other glycols such as xylitol and/or propanediol, etc.), from 99/1 to 1/99 (w/w), advantageously in water as sole solvent. Thus, in one particular embodiment, the extract is a leaf extract prepared in water as sole solvent.

In particular, the extract is obtained by aqueous extraction. For the purpose of the present invention, "extract obtained by aqueous extraction" is intended to mean any extract obtained by extraction with an aqueous solution containing more than 60% by weight, advantageously at least 70% by weight, in particular at least 80% by weight, more particularly at least 90% by weight, particularly at least 95% by weight, of water relative to the total weight of the aqueous solution, even more advantageously not containing glycol and in particular not containing alcohol, more particularly only containing water.

In one alternative embodiment, the extract is obtained by extraction in a mixture of propanediol and water in the respective proportion (80, 20; w/w).

In another alternative embodiment of the invention, the extraction may moreover be carried out in the presence of a nonionic surfactant, preferentially chosen from lauryl glucoside sold under the name Plantacare® 1200UP by BASF or else caprylyl/capryl glucoside (Plantacare® 810 UP), preferentially caprylyl/capryl glucoside (Plantacare® 810 UP). The concentration by weight of the nonionic surfactant may be between 0.5% and 5%, advantageously between 0.5 and 1%, more advantageously it will be 1% by weight relative to the total weight of the extract.

The extract can be obtained by extraction of an amount of from 0.1% to 10% by weight of fresh material or solids, preferentially solids, of at least one part of the N. lappaceum plant relative to the total weight of the solvent/plant mixture (w/w). Preferentially, the extract is obtained by extraction of an amount of from 1% to 10% by weight, advantageously from 5% to 10%, more advantageously of 10% by weight of solids of at least one part of the plant, relative to the total weight of the mixture consisting of the solvent, preferentially water, and of the plant (w/w). In one particular embodiment of the invention, the extract will be obtained from an amount of 10% by weight of at least one part of the plant relative to the total weight of the solvent/plant mixture (w/w), then concentrated to 20%. Preferentially, the part of the plant will then be the seeds.

Thus, in one advantageous embodiment of the invention, the extract is obtained by maceration in water as sole solvent, of an amount of 10% by weight of dried leaves of the N. lappaceum plant relative to the total weight of leaves and water, at a temperature of 80° C., for a period of 1 hour, under the conditions described in example 1a). The crude extract obtained is then decanted, centrifuged and then filtered. The extract obtained may optionally be dried and will be in powder form.

In another embodiment, the extract is obtained by maceration from an amount of 5% by weight of dried leaves of the N. lappaceum plant relative to the total weight of leaves and water, at a temperature of 80° C., for a period of 1 hour, under the conditions described in example 1b). The crude extract obtained is then decanted, centrifuged and then filtered.

In yet another embodiment of the invention, the extract is obtained by maceration from an amount of 10% by weight of dried branch of the N. lappaceum plant relative to the total weight of branch and water, at ambient temperature, that is to say at a temperature of 20° C., for a period of 2 hours, under the conditions described in example 1c). Advantageously in this case, the extraction is carried out in the presence of a concentration by weight of 1% of caprylyl/capryl glucoside (Plantacare® 810 UP). The crude extract obtained is then decanted, centrifuged and then filtered.

In a $4^{th}$ embodiment of the invention, the extraction is carried out by maceration from an amount of 10% by weight of dried leaves of N. lappaceum in a propanediol/water mixture (80, 20; v/v) at a temperature of 80° C. for a period of 1 hour, under the conditions described in example 1 d). The crude extract obtained is then decanted, centrifuged and then filtered.

In a $5^{th}$ embodiment of the invention, the extraction is carried out by extraction in water under subcritical conditions, of an amount of 10% by weight of dried leaves of N. lappaceum in a pressure extraction autoclave, at a temperature of 250°, under a pressure of 250 bar under the conditions described in example 1e). The crude extract obtained is then decanted, centrifuged and then filtered. The extract obtained may optionally be dried.

In a $6^{th}$ embodiment of the invention, the extraction will be carried out by maceration of an amount of 10% by weight of the fruit pulp relative to the total weight of pulp and water as sole solvent, at a temperature of 80° C., for a period of 1 hour, under the conditions described in example 1f). Alternatively, the extraction of pulp may be carried out starting from an amount of 10% by weight of pulp, in a propanediol/water mixture (80, 20; v/v) at a temperature of 80° C. for a period of 1 hour. In yet another alternative embodiment, the extraction of pulp may be carried out by extraction in water under subcritical conditions. The crude extract obtained is then decanted, centrifuged and then filtered.

In a $7^{th}$ embodiment of the invention, the extraction will be carried out by maceration of an amount of 10% of seeds by weight relative to the total weight of the seeds and water as sole solvent, at ambient temperature, that is to say at 20° C., for a period of 2 hours, under the conditions described in example 1g). Alternatively, the extraction of seeds may be carried out starting from an amount of 10% by weight of seeds, in a propanediol/water mixture (80, 20; v/v) at a temperature of 80° C. for a period of 1 hour. In yet another alternative embodiment, the extraction of seeds may be carried out by extraction in water under subcritical conditions. The crude extract obtained is then decanted, centrifuged and then filtered.

The extract obtained and used according to the invention may then be centrifuged and/or filtered and/or distilled to recover the soluble fraction, preferentially the water-soluble fraction. Preferentially, the supernatant obtained is then filtered, advantageously at a cut-off threshold of 0.45 μm. Additional decolorizing and/or deodorizing steps can be carried out on the extract at any stage of the extraction and according to the techniques known to those skilled in the art. In particular, the extract may be decolorized with activated carbon.

The extract can then be concentrated by evaporation of the solvent or dried, for example by lyophilization or by spray-drying in the presence of maltodextrins. The extract will then be in powder form.

Thus, in one preferential embodiment of the invention, the extract obtained will be spray-dried in the presence of a concentration by weight of maltodextrins of between 20% and 90%, preferentially between 40% and 80%, more preferentially from 70% to 80% relative to the total weight of the powder obtained.

In one particular embodiment of the invention, in particular for use thereof in dermatology, the N. lappaceum extract obtained is sterilized.

The extract can be used alone in the form of a cosmetic or dermatological ingredient, or in a cosmetic or dermatological composition, comprising at least one cosmetically or dermatologically acceptable excipient.

When it is used alone in the form of a cosmetic or dermatological ingredient, it is preferentially solubilized in and/or diluted in a solvent, in particular a polar solvent, such as water, an alcohol, a polyol, a glycol, such as pentylene glycol and/or butylene glycol and/or hexylene glycol and/or caprylyl glycol, or a mixture thereof, preferentially an aqueous-glycolic mixture, more preferentially containing a glycol chosen from hexylene glycol, caprylyl glycol and mixtures thereof. Advantageously, the extract obtained is diluted and/or soluble in an aqueous solution containing hexylene glycol, in particular containing between 0.1% and 10% by weight of hexylene glycol, preferentially between 0.5% and 5% by weight of hexylene glycol, relative to the total weight of the aqueous solution. Advantageously, the extract obtained is diluted and/or soluble in an aqueous solution containing caprylyl glycol, in particular containing between 0.01% and 5% by weight of caprylyl glycol, preferentially between 0.1% and 1% by weight of caprylyl glycol, relative to the total weight of the aqueous solution. In particular, the aqueous solution in which the *N. lappaceum* extract is solubilized according to the invention comprises xanthan gum, in particular between 0.01% and 5% by weight of xanthan gum, relative to the total weight of the aqueous solution, more particularly between 0.1% and 1% by weight of xanthan gum relative to the total weight of the aqueous solution.

Advantageously, the solution in which the *N. lappaceum* extract is solubilized according to the invention comprises hexylene glycol, caprylyl glycol and xanthan gum.

In one alternative embodiment of the invention, the extract will be solubilized in an aqueous solution comprising glycerin at a concentration by weight relative to the total weight of the cosmetic ingredient of from 50% to 85%, advantageously from 60% to 80%, more advantageously of 79%, biopropanediol at a concentration by weight relative to the total weight of the cosmetic ingredient of from 5% to 20%, advantageously of 10%, and water.

The extract can also be present in a cosmetic composition further comprising at least one cosmetically acceptable excipient, The term "acceptable" is intended to mean a cosmetic excipient or excipient non-irritating to the skin, which does not induce an allergic response and is chemically stable.

A subject of the present invention therefore relates to the use of the extract of the *N. lappaceum* plant according to the invention in a cosmetic composition for increasing the firmness and/or elasticity of the skin and/or mucous membranes, by increasing type I and/or type V collagen, preferentially type I collagen, LOX-L, fibulin-5, emilin-1 and/or fibrillin, preferentially fibrillin-1, gene and/or protein expression, and/or by decreasing CYR61 expression, in the skin and/or mucous membranes.

The cosmetic composition comprising the *N. lappaceum* extract according to the invention may be applied, preferentially topically, to all or part of the body and/or the face where an increase in firmness and/or elasticity is desired, preferentially the legs, thighs, arms, stomach, bust, neck, all or part of the face, preferentially the cheeks, forehead, chin, lips, area around the lips, area around the eyes, the "T" zone of the face.

In one embodiment of the invention, the extract is present in the cosmetic or dermatological composition at a concentration of $1\times10^{-4}$% to 10%, preferentially from $1\times10^{-4}$% to 5%, and even more preferentially from $1\times10^{-3}$% to 3% by weight, relative to the total weight of the composition. The excipient(s) may be chosen from surfactants and/or emulsifiers, preservatives, buffers, chelating agents, denaturing agents, opacifiers, pH adjusters, reducing agents, stabilizers, thickeners, gelling agents, film-forming polymers, fillers, mattifying agents, gloss agents, pigments, dyes, fragrances and mixtures thereof. The CTFA (Cosmetic Ingredient Handbook, Second Edition (1992)) describes various cosmetic excipients suitable for use in the present invention.

Advantageously, the excipient(s) are chosen from the group comprising polyglycerols, esters, cellulose polymers and derivatives, lanolin derivatives, phospholipids, lactoferrins, lactoperoxidases, saccharose-based stabilizers, vitamin E and its derivatives, xanthan gums, natural and synthetic waxes, vegetable oils, triglycerides, unsaponifiables, phytosterols, silicones, protein hydrolyzates, betaines, aminoxides, plant extracts, saccharose esters, titanium dioxides, glycines, and parabens, and more preferably from the group consisting of steareth-2, steareth-21, glycol-15 stearyl ether, cetearyl alcohol, phenoxyethanol, methylparaben, ethylparaben, propylparaben, butylparaben, butylene glycol, caprylyl glycol, natural tocopherols, glycerin, dihydroxycetyl sodium phosphate, isopropyl hydroxyketyl ether, glycol stearate, triisononanoine, octyl cocoate, polyacrylamide, isoparaffin, laureth-7, a carbomer, propylene glycol, hexylene glycol, glycerol, bisabolol, dimethicone, sodium hydroxide, PEG 30-dipolyhydroxysterate, capric/caprylic triglycerides, cetearyl octanoate, dibutyl adipate, grape seed oil, jojoba oil, magnesium sulfate, EDTA, a cyclomethicone, xanthan gum, citric acid, sodium lauryl sulfate, waxes and mineral oils, isostearyl isostearate, propylene glycol dipelargonate, propylene glycol isostearate, PEG 8, beeswax, glycerides of hydrogenated palm heart oil, lanolin oil, sesame oil, cetyl lactate, lanolin alcohol, castor oil, titanium dioxide, lactose, saccharose, low density polyethylene, an isotonic saline solution, and mixtures thereof.

The cosmetic composition according to the invention may be chosen from an aqueous or oily solution, a cream or an aqueous gel or an oily gel, especially a shower gel, a milk, an emulsion, a microemulsion or a nanoemulsion, which is especially oil-in-water or water-in-oil or multiple or silicone-based, a mask, a serum, a lotion, a liquid soap, a dermatological bar, an ointment, a foam, a patch, an anhydrous product, which is preferably liquid, pasty or solid, for example in the form of makeup powders, a rod or a stick, in particular in the form of a lipstick. Advantageously, it is a cream or a serum.

The composition used according to the invention may also contain cosmetic active ingredients leading to a complementary or synergistic effect, such as anti-aging active agents. Among these, mention may be made of active agents that stimulate the synthesis of macromolecules of the dermis or prevent the degradation thereof, agents that stimulate keratinocyte proliferation, soothing agents, moisturizing agents, or else agents that act on regulating the size of pores and/or the opening thereof.

Among the anti-aging active agents, mention will be made of:
- an agent which stimulates fibronectin synthesis, in particular a corn extract, such an extract being especially sold by BASF Beauty Care Solutions France under the name Deliner™, and the palmitoyl pentapeptide sold by the company Sederma under the trade name Matrixil®;
- an agent which stimulates the formation of collagen fibers, such as an *Origanum majorana* extract sold under the name Dermagenist™ by BASF Beauty Care Solutions France;
- an agent which stimulates perlecan and dystoglycan expression in the extracellular matrix and/or in the epithelial basal membrane, such as for example a

*Polygonum bistorta* extract sold under the name Perlaura™ BASF Beauty Care Solutions France, an agent which protects extracellular matrix fibroblast growth factor (FGF2) against degradation thereof and/or denaturation thereof, especially a *Hibiscus abelmoscus* extract as described in the patent application in the name of BASF Beauty Care Solutions France filed under number FR0654316 and sold by BASF Beauty Care Solutions France under the name Linefactor™ and/or an agent which stimulates fibroblast growth, for example a fermented soybean extract containing peptides, known as Phytokine™ sold by BASF Beauty Care Solutions France and also described in patent application EP 1 119 344 B1 (Laboratoires Expanscience), and preferentially a combination of these two extracts;

an agent which stimulates laminin synthesis, in particular a biotechnology-modified malt extract, such an extract being especially sold by BASF Beauty Care Solutions France under the name Basaline™;

an agent which stimulates hyaluronane synthase 2 (HAS2) expression and/or activity, such as the plant extracts described in patent application FR 2 893 252 and in particular an aqueous extract of Galanga (*Alpinia galanga*) and sold by BASF Beauty Care Solutions France under the name Hyalufix™;

an agent which stimulates lysyl oxidase-like (LOXL) synthesis, such as a *Geophila cordifolia* extract and those described in patent application FR 2 855 968, and in particular a dill extract and sold by BASF Beauty Care Solutions France under the name Lys'lastine™;

an agent which stimulates intracellular ATP synthesis, in particular an extract of the alga *Laminaria digitata;* an active agent which stimulates glycosamonoglycan synthesis, such as a milk fermentation product;

an active agent which stimulates collagen, such as retinol and/or vitamin C;

an active agent which inhibits metalloproteases (MMPs) such as more particularly MMPs 1, 2, 3 and 9, such as retinoids and derivatives, oligopeptides and lipopeptides, lipoamino acids, the extract of *Argania spinoso* leaves sold by BASF Beauty Care Solutions France SAS under the name Arganyl™; lycopene; isoflavones, quercetin, kaempferol, apigenin;

a swelling agent, especially the hyaluronic acid filling spheres sold by BASF Beauty Care Solutions France (Hyaluronic Filling Spheres™);

an agent for increasing the expression of LOX, for increasing the architecture of the epidermis, such as, for example, a *Cichorium intybus* extract, sold under the name LOX-AGE™ by BASF Beauty Care Solutions France;

an agent for increasing collagen deglycation and/or increasing the expression of type I collagen, such as a combination of an extract of *Salvia miltiorrhiza* leaves and of niacinamide, sold by BASF Beauty Care Solutions France under the name CollRepair™;

an agent which stimulates lumican and collagen synthesis, such as a synthetic acetyl Gln Asp Val His tetrapeptide sold by BASF Beauty Care Solutions France under the name Dermican™ and described in patent application WO 2005/120554;

an agent for protecting and stimulating elastin and collagen, such as the extract of *Manilkara multinervis* leaves sold by BASF Beauty Care Solutions France under the name Elestan™ and the extract of *Eperua falcata* root sold by BASF Beauty Care Solutions France under the name Eperuline™;

an anti-pigment-spot agent, in particular acting by inhibiting melanin synthesis, such as the synergistic complex of *Pisum sativum* extract and sucrose dilaurate, sold by BASF Beauty Care Solutions France under the name Actiwhite™, or hydroxyphenoxy propionic acid sold by BASF Beauty Care Solutions France under the name Radianskin™;

an agent which stimulates the firmness and elasticity of the skin, such as a *Khaya senegalensis*, extract sold by the applicant under the name Collalift® 18.

The agents which stimulate keratinocyte proliferation, preferentially of use in the composition according to the invention, comprise in particular retinoids such as retinol and esters thereof, including retinyl paimitate, and phloroglucinol. The agents which stimulate keratinocyte differentiation comprise, for example, minerals such as calcium and lignans such as secoisolariciresinol and also the *Achillea millefollium* extract sold under the name Neurobiox™ by BASF Beauty Care Solutions France.

As soothing agents preferentially of use in the composition according to the invention, mention may be made of: pentacyclic triterpenes, ursolic acid and salts thereof, oleanolic acid and salts thereof, betulinic acid and salts thereof, salicylic acid salts and in particular zinc salicylate, bisabolol, allantoin, omega-3 unsaturated oils, cortisone, hydrocortisone, indomethacin and betamethasone, anti-inflammatory active agents, and especially those described in application FR 2 847 267, in particular the *Pueraria lobata* root extract sold under the name Inihipase® by BASF Beauty Care Solutions France SAS, *Theobroma cacao* extracts.

Among the agents acting on the regulation of pore size and/or the opening thereof and/or on sebum production, mention may be made by way of example of a *Cichorium intybus* extract sold under the name LOX-AGE™ by BASF Beauty Care Solutions France, or synthetic sarcosine sold under the name Mat-XS™ Clinical and/or an *Orthosiphon stamineus* extract as described in patent application WO2010/063674 in the name of BASF Beauty Care Solutions France and sold under the name MAT XS™ Bright.

As moisturizing agents preferentially of use in the composition according to the invention, mention may be made of: a combination of pullulan, of sodium hyaluronate and of sodium alginate, such as that sold by BASF Beauty Care Solutions France under the name PatcH$_2$O™.

Another subject of the invention also relates to a cosmetic care method comprising the application, topically or orally, preferentially topically, of the extract according to the invention or of a cosmetic composition comprising it to increase the firmness and/or the elasticity of the skin and/or mucous membranes.

Thus, the cosmetic care method according to the invention is for increasing type I and/or type V collagen, preferentially type I collagen, gene and/or protein expression, and/or decreasing CYR61 expression, in the skin and/or mucous membranes to increase the firmness of the skin and/or mucous membranes.

Another subject of the invention relates to a cosmetic care method which comprises the topical or oral application, preferentially topical application, of the *N. lappaceum* extract according to the invention or of a cosmetic composition comprising it, for increasing the elasticity of the skin and/or mucous membranes, by increasing fibrillin, preferentially fibrillin-1, LOX-L, fibulin-5 and/or emilin-1, more preferentially fibrillin-1, gene and/or protein expression, and advantageously protein expression, in the skin and/or mucous membranes.

In one embodiment of the invention, the method comprises the topical application to all or part of the skin of the body and/or face where an increase in firmness and/or elasticity is desired, preferentially the legs, thighs, arms, stomach, bust, neck, all or part of the face, preferentially the cheeks, forehead, chin, lips, area around the lips, area around the eyes, the "T" zone of the face, of the extract according to the invention or a cosmetic composition comprising it.

Finally, another subject of the present invention relates to the N. lappaceum extract for use thereof, topically or orally and preferentially topically, alone or in a pharmaceutical composition, preferentially a dermatological composition, comprising it, in the prevention and/or treatment of pathological conditions involving a loss of collagen, preferentially type I collagen, protein and/or gene expression and/or a pathological loss of firmness of the skin and/or mucous membranes, such as rosacea or telangiectasia.

Finally, another subject of the present invention relates to the N. lappaceum extract for use thereof, topically or orally and preferentially topically, alone or in a pharmaceutical composition, preferentially a dermatological composition, comprising it, in the prevention and/or treatment of pathological conditions involving a loss of fibrillin, preferentially type I fibrillin, protein and/or gene expression and/or a pathological loss of elasticity of the skin and/or mucous membranes, such as solar elastosis, cutis laxa disease and/or stretch marks.

In one embodiment of the invention, the extract is included in the dermatological or pharmaceutical composition comprising, moreover, at least one dermatologically or pharmaceutically acceptable excipient, at a concentration of from $1\times10^{-4}$% to 10%, preferentially from $1\times10^{-4}$% to 5%, and more preferentially from $1\times10^{-3}$% to 3% by weight, relative to the total weight of the composition.

Examples referring to the description of the invention are presented below. These examples are given for illustrative purposes and in no way limit the scope of the invention. Each of the examples has a general scope. The examples are an integral part of the present invention, and any feature appearing to be novel over any prior art whatsoever, from the description taken in its entirety, including the examples, is an integral part of the invention.

EXAMPLES

Example 1: Preparation of Various N. lappaceum Extracts According to the Invention Example 1a) The extract was obtained by maceration in water as sole solvent, of an amount of 10% by weight of dried leaves of the N. lappaceum plant relative to the total weight of leaves and water as sole solvent, at a temperature of 80° C., for a period of 1 hour. The crude extract was decanted, centrifuged and then filtered. This extract may then be subsequently dried.

Example 1b) The extract vas obtained by maceration starting from an amount of 5% by weight of leaves of the N. lappaceum plant relative to the total weight of dried leaves and water as sole solvent, at a temperature of 80° C., for a period of 1 hour. The crude extract was centrifuged and then filtered.

Example 1c) The extract was obtained by maceration starting from an amount of 10% by weight of dried branches of the N. lappaceum plant relative to the total weight of branches and water as sole solvent, at ambient temperature, that is to say at a temperature of 20° C., for a period of 2 hours in the presence of a concentration by weight of 1% of caprylyl/capryl glucoside (Plantacare® 810 UP). The crude extract was decanted, centrifuged and then filtered.

The extracts obtained in examples 1a) to 1c) were then concentrated by evaporation of the solvent and dried by spray drying in the presence of maltodextrins. These extracts are in powder form.

Example 1d) The extraction was carried out by maceration starting from an amount of 10% by weight of dried leaves of N. lappaceum in a propanediol/water mixture (80, 20; w/w) at a temperature of 80° C. for a period of 1 hour. The crude extract was decanted, centrifuged and then filtered.

Example 1e) The extraction was carried out starting from an amount of 10% by weight of dried leaves of N. lappaceum in water under subcritical conditions, in a pressure extraction autoclave, at a temperature of 250° C., under a pressure of 250 bar. The crude extract was decanted, centrifuged and then filtered.

Example 1f) The extraction was carried out by maceration in water as sole solvent, starting from an amount of 10% by weight of fruit pulp of N. lappaceum relative to the total weight of the pulp and water, at a temperature of 80° C. for a period of 1 hour. The crude extract was decanted, centrifuged and then filtered.

Example 1g) The extraction was carried out by maceration in water as sole solvent of an amount of 10% of seeds by weight relative to the total weight of the seeds and water, at ambient temperature, that is to say 20° C., for a period of 2 hours. The crude extract was decanted, centrifuged and then filtered.

Example 1h) The extract was obtained by maceration starting from an amount of 10% by weight of dried branch of the N. lappaceum plant relative to the total weight of branch and water as sole solvent, at a temperature of 80° C., for a period of 1 hour. The crude extract was decanted, centrifuged and then filtered.

Example 2: Increase in Type I Collagen Expression in the Presence of Various N. lappaceum Extracts According to the Invention Protocol: "normal" human fibroblasts, that is to say fibroblasts exhibiting no pathological condition, from a 34-year-old healthy female donor, were cultured in a defined medium (FGM) for a period of 48 hours in the presence of 2 different final concentrations of various N. lappaceum extracts, then the cell medium was removed. The same culture medium without addition of extract according to the invention was used as a control (Control). The cell layer obtained was lyzed with an ammonium hydroxide solution.

The type I collagen was assayed using the lysate obtained with an anti-collagen I antibody, used at 500 ng/ml in a buffer solution (PBS). After a period of 60 minutes, a secondary antibody used at 40 ng/ml was applied for a period of 60 minutes. After washing, a revealing solution was added and the fluorescence was measured (ENVision, PerkinElmer). The fluorescence results were standardized relative to the fluorescence obtained with the same cell medium in the absence of the N. lappaceum extract (Control) and were related to the amount of DNA obtained under each condition. The results presented correspond to the mean of 6 assays (n=6). (SD: Standard deviation).

Results:

TABLE 1

|  | MEAN | SD |
|---|---|---|
| Control | 100 | 14 |
| Extract of N. lappaceum leaves a 1% (w/v medium) prepared according to ex. 1a) | 290 | 72 |
| Extract of N. lappaceum seeds at 10% (w/v medium) prepared according to ex. 1g) | 103 | 5 |
| Extract of N. lappaceum branch at 10% (w/v medium) prepared according to ex. 1h) | 94 | 10 |
| Extract of N. lappaceum pulp at 10% (w/v medium) prepared according to ex. 1f) | 95 | 8 |

Conclusion: the extract of N. lappaceum leaves increased the type I collagen protein expression by at least 104% and up to 686% in the fibroblasts analyzed.

Example 3) Increase in Type V Collagen Expression in the Presence of Various N. lappaceum Extracts Protocol: "normal" human fibroblasts, that is to say fibroblasts exhibiting no pathological condition, from a 34-year-old healthy female donor, were cultured in a defined medium (FGM) for a period of 48 hours in the presence of different final concentrations of various N. lappaceum extracts, then the cell medium was removed. The same culture medium without addition of extract according to the invention was used as a control (Control). The cell layer obtained was lyzed with ammonium hydroxide solution, and then the type V collagen was assayed with an anti-collagen V antibody, diluted to 1/4000 in buffer solution (PBS). After a period of 60 minutes, a secondary antibody diluted to 1/25000 was applied for a period of 60 minutes. After washing, a revealing solution was added and the fluorescence was measured (ENVision, PerkinElmer). The fluorescence results were standardized relative to the fluorescence obtained with the same cell medium in the absence of the N. lappaceum extract (Control) and were related to the amount of DNA obtained under each condition. The results presented correspond to the mean of 3 assays (n=3) (SD: Standard deviation).
Results:

TABLE 2

|  | MEAN | SD |
|---|---|---|
| Control | 100 | 5 |
| Extract of N. lappaceum leaves 1% (w/v medium) prepared according to ex. 1a) | 231 | 39 |
| Extract of N. lappaceum branch 0.1% (w/v medium) prepared according to ex. 1c) | 176 | 24 |
| Extract of N. lappaceum seeds 1% (w/v medium) prepared according to ex. 1g) | 134 | 25 |
| Extract of N. lappaceum pulp 0.5% (p/v medium) prepared according to example 1f) | 131 | 10 |

Conclusion: the N. lappaceum extracts increased type V collagen protein expression by at least 4% and up to at least 400% in the normal fibroblasts analyzed, demonstrating their properties of increasing the firmness of the skin and mucous membranes.

Example 4: Increase in Fibrillin-1 Expression in the Presence of Various N. lappaceum Extracts Protocol: "normal" human fibroblasts, that is to say fibroblasts exhibiting no pathological condition, from a 34-year-old healthy female donor, were cultured in a defined medium (FGM) for a period of 48 hours in the presence of 2 different final concentrations of the N. lappaceum extract, then the cell medium was removed. The same culture medium without the addition of extract was used as a control (Control). The cells were subsequently harvested and then lyzed with a specific lysis buffer in order to carry out the immunolocalization (Western Blot). The protein concentration was determined by the BCA method. The proteins were identified by capillary electrophoresis (ProteinSimple, USA) using an anti-fibrillin primary antibody and immunolocalized using a peroxidase-coupled conjugated secondary antibody. The results were quantified using the Compass Software (version 2.7.1 (ProteinSimple)).
Results:

TABLE 3

|  | MEAN | SD |
|---|---|---|
| Control | 100 | 9 |
| Extract of N. lappaceum leaves 1% (p/v medium) prepared according to example 1a) | 239 | 56 |
| Extract of N. lappaceum branches 0.1% (p/v medium) prepared according to example 1c) | 148 | 1 |
| Extract of N. lappaceum seeds 1% (p/v medium) prepared according to example 1g) | 272 | 95 |
| Extract of N. lappaceum pulp 0.5% (p/v medium) prepared according to example 1f) | 166 | 18 |

Conclusion: the results showed an increase of at least 30% and up to at least 200% of fibrillin-1 protein expression in the normal human fibroblasts, showing its ability to increase the elasticity of the skin and/or mucous membranes.

Example 5: Decrease in CYR61 Protein Expression in the Presence of an N. lappaceum Extract Protocol: "normal" human fibroblasts, that is to say fibroblasts exhibiting no pathological condition, from a 34-year-old healthy female donor, were cultured in a defined medium (FGM) for a period of 48 hours in the presence of different final concentrations of N. lappaceum extracts, then the cell medium was removed. The same culture medium without addition of extract according to the invention was used as a control (Control). The supernatants were then recovered for analysis. The protein concentration was determined by BCA assay (BiCinchoninic acid Assay). The protein expression was measured by Western Blot (n=4) (SallySue®, ProteinSimple®). The CYR61 protein of interest was detected by capillary electrophoresis (Antibody AbCam (ab24448)e diluted to 1/50) then revealed with a horseradish peroxidase-coupled secondary antibody and a chemiluminescent substrate. The chemiluminescent signal was then detected and quantified (Compass® version 23.1 (ProteinSimple®)).
Results:
The results are expressed as relative percentages with respect to the level of CYR61 protein expression in the supernatants of non-treated fibroblasts (Control).

TABLE 4

|  | MEAN | SD |
|---|---|---|
| Control | 100 | 7.8 |
| Dried extract of N. lappaceum leaves prepared according to example 1a) ($4 \times 10^{-3}$ w/v medium) | 79.4 | 8.2 |
| Dried extract of N. lappaceum leaves prepared according to example 1a) ($8 \times 10^{-3}$ w/v medium) | 52.4 | 7.9 |

Conclusion: the extract of *N. lappaceum* leaves showed its ability to decrease CYR61 protein expression. The extract is therefore active on the firmness of the skin and/or mucous membranes.

Example 6: Example of Cosmetic Ingredient

The amounts indicated are as percentage by weight relative to the total weight of the cosmetic ingredient.

Example 6a)

| *N. lappaceum* extract Ex. 1a) to 1e) | 1-20% (w/w) |
|---|---|
| Maltodextrins | 80-99% (w/w) |

Example 6b)

| *N. lappaceum* extract Ex. 1a) to 1e) | 1% |
|---|---|
| Glycerin | 79% |
| Biopropanediol | 10% |
| Water | 10% |

Example 7: Examples of Cosmetic Compositions

The compositions below are prepared according to methods known to those skilled in the art, in particular as regards the various phases to be mixed together.

The cosmetic ingredient is prepared according to example 6 above. The amounts indicated are as percentage by weight relative to the total weight of the composition.

7a)

| Cosmetic ingredient* | 0.2-0.3 |
|---|---|
| EDTA | 0.05 |
| Steareth-2 | 2.00 |
| Steareth-21 | 2.50 |
| Cetearyl alcohol | 1.00 |
| Propylheptyl caprylate | 15.00 |
| Sodium hydroxide (30% in solution) | 0.10 |
| Mixture of phenoxyethanol, chlorphenesin, benzoic acid, Butylene glycol, sorbic acid (Germazide ™ PBS) | 1.25 |
| Mixture of polyacrylate-X, isohexadecane and polysorbate 60 (Sepigel ™ SMS 60) | 4.00 |
| Water | qs 100 |

7b)

| Cosmetic ingredient* | 0.2-0.3 |
|---|---|
| EDTA | 0.05 |
| Steareth-2 | 2.00 |
| Steareth-21 | 2.50 |
| Cetearyl alcohol | 1.00 |
| Propylheptyl caprylate | 15.00 |
| Sodium hydroxide (30% in solution) | 0.10 |
| Mixture of phenoxyethanol, chlorphenesin, benzoic acid, Butylene glycol, sorbic acid (Germazide ™ PBS) | 1.25 |
| Mixture of polyacrylate-X, isohexadecane and polysorbate 60 (Sepigel ™ SMS 60) | 4.00 |
| Water | qs 100 |

7c)

Methods known to those skilled in the art are used to mix together the different phases A, B, C and D below in order to prepare a composition according to the present invention. The proportions are expressed as %.

Phase A

| Glyceryl stearate, PEG-100 Stearate | 4.00 |
|---|---|
| Pentaerythrityl distearate | 1.50 |
| Cetearyl Isononanoate | 3.00 |
| Propylheptyl caprylate | 5.00 |
| Coco caprylate | 2.00 |
| Dicaprylyl carbonate | 3.00 |
| Dimethicone | 1.00 |

Phase B

| Water | 64.43 |
|---|---|
| Propylene glycol, phenoxyethanol, chlorphenesin, methylparaben | 1.00 |
| Glycerin | 1.57 |
| Xanthan gum | 0.20 |
| Butylene glycol | 2.00 |
| Sodium hydroxide, water | 0.15 |

Phase C

| Carbomer | 0.15 |
|---|---|
| Water | 10 |

Phase D

| *N. lappaceum* extract obtained according to example 6a) | 1.00 |
|---|---|

The invention claimed is:

1. A method of increasing the firmness and/or elasticity of the skin and/or mucous membranes comprising administering an effective amount of a *Nephelium lappaceum* extract or a cosmetic composition comprising the *Nephelium lappaceum* extract to a human subject in need thereof, wherein the *Nephelium lappaceum* extract is a leaf extract obtained by extracting with water as sole solvent in an amount of 1-20% by weight based on the total weight of the water, at a temperature of 60 to 90° C. for a time of 30 minutes to 12 hours followed by drying, wherein the *Nephelium lappaceum* extract or the cosmetic composition is topically applied, and wherein the *Nephelium lappaceum* extract is present in the cosmetic composition at a concentration of from $1 \times 10^{-4}$% to 3% by weight, relative to the total weight of the composition.

2. The method of claim 1, wherein the firmness and/or elasticity of the skin and/or mucous membranes is increased.

3. The method of claim 1, wherein the firmness of the skin and/or mucous membranes is increased.

4. The method of claim 1, wherein the *Nephelium lappaceum* extract increases gene and/or protein expression of type I and/or type V collagen.

5. The method of claim 1, wherein the *Nephelium lappaceum* extract increases gene and/or protein expression of LOX-L, fibulin-5, emilin-1 and/or fibrillin-1.

6. The method of claim 1, wherein the *Nephelium lappaceum* extract and/or the cosmetic composition comprising the *Nephelium lappaceum* extract is topically applied on all or part of a human body selected from the group consisting of leg, thigh, arm, stomach, bust, neck, face, cheek, forehead, chin, lips, area around the lips, area around the eyes, the T zone of the face, and combinations thereof.

7. The method of claim 1, wherein the *Nephelium lappaceum* extract is obtained by aqueous extraction under subcritical conditions.

8. The method of claim 1, wherein the extract is spray-dried in the presence of a concentration by weight of maltodextrins of between 20% and 90%, between 40% and 80%, or from 70% to 80%, relative to the total weight of the powder obtained.

9. The method of claim 1, wherein the cosmetic composition comprising the *Nephelium lappaceum* extract further comprises at least one acceptable cosmetic excipient.

10. The method of claim 1, wherein the *Nephelium lappaceum* extract is obtained by aqueous extraction at 70° C. to 85° C. for 1 to 5 hours.

* * * * *